(12) United States Patent
Kim et al.

(10) Patent No.: US 7,680,638 B2
(45) Date of Patent: Mar. 16, 2010

(54) HUMAN-CLOTHING-ENVIRONMENT SIMULATOR

(75) Inventors: Eunae Kim, Seoul (KR); Shinjung Yoo, Seoul (KR)

(73) Assignee: Yonsei University, Seoul (KR)

( * ) Notice: Subject to any disclaimer, the term of this patent is extended or adjusted under 35 U.S.C. 154(b) by 455 days.

(21) Appl. No.: 10/896,876

(22) Filed: Jul. 23, 2004

(65) Prior Publication Data
US 2004/0260524 A1  Dec. 23, 2004

(30) Foreign Application Priority Data
Mar. 27, 2003  (KR) .................... 10-2003-0019136

(51) Int. Cl.
*G06G 7/48* (2006.01)
(52) U.S. Cl. .................. 703/6; 703/1; 703/7; 702/1; 702/127; 702/130; 702/131; 374/100; 374/109; 374/132; 374/134; 374/145
(58) Field of Classification Search .................. 703/6, 703/1, 7; 702/1, 127, 130, 131; 374/100, 374/109, 132, 134, 145
See application file for complete search history.

(56) References Cited

U.S. PATENT DOCUMENTS

| | | | | |
|---|---|---|---|---|
| 4,537,822 A | * | 8/1985 | Nanri et al. ................. | 428/212 |
| 4,890,932 A | * | 1/1990 | Kobayashi et al. .......... | 374/109 |
| 5,409,382 A | * | 4/1995 | Donnelly et al. ............ | 434/267 |
| 5,436,852 A | * | 7/1995 | Kon ........................... | 700/276 |
| 5,624,729 A | * | 4/1997 | Cohen et al. ................. | 428/90 |
| 5,669,610 A | * | 9/1997 | Salyers ....................... | 273/407 |
| 5,749,259 A | * | 5/1998 | Hamouda et al. ............. | 73/159 |
| 5,888,914 A | * | 3/1999 | Katz ........................... | 442/184 |
| 5,940,784 A | * | 8/1999 | El-Husayni ................. | 702/130 |
| 6,030,116 A | * | 2/2000 | Yanai et al. ................. | 374/142 |

(Continued)

OTHER PUBLICATIONS

C. Huizenga, Z. Hui, and E. Arens, "A Model of Human physiology and comfort for assessing complex thermal environments" 2001 Elsevier Science Ltd, pp. 691-699.*

(Continued)

*Primary Examiner*—Kamini S Shah
*Assistant Examiner*—Kibrom Gebresilassie
(74) *Attorney, Agent, or Firm*—Rothwell, Figg, Ernst & Manbeck, PC

(57) ABSTRACT

Provided is a man-clothing-environment (MCE) simulator quantitatively measuring properties of clothes to transfer heat and moisture between human skin and an external environment. The MCE simulator includes a hot chamber providing a high-temperature environment, a cold chamber providing a low-temperature environment, a skin model selectively coupled to the hot chamber or the cold chamber while being vertically erect, a water supplier supplying water to a hot plate included in the skin model, and a controller controlling the hot chamber, the cold chamber and the skin model, and processing data on temperature and humidity measured by sensors. The skin model includes the hot plate receiving heat and water while being vertically erect and simulating human skin, a ring-shaped frame coupled to a side of the hot plate and supporting a fabric to be separated from the side of the hot plate, and the sensors measuring temperature and humidity inside and outside the fabric. The MCE simulator may properly simulate a state of wearing clothes by employing the vertical skin model and effectively measure properties of clothes to transfer heat and moisture according to rapid changes in an external environment by including the hot and cold chambers.

22 Claims, 7 Drawing Sheets

U.S. PATENT DOCUMENTS

| | | | | |
|---|---|---|---|---|
| 6,046,119 | A | * | 4/2000 | Kaibe et al. .................... 442/76 |
| 6,088,949 | A | * | 7/2000 | Nicosia et al. ................. 43/107 |
| 6,272,770 | B1 | * | 8/2001 | Slutsky et al. ................. 34/596 |
| 6,312,155 | B1 | * | 11/2001 | Stool et al. .................... 374/45 |
| 6,408,256 | B1 | * | 6/2002 | Hittle et al. ................. 702/130 |
| 6,698,663 | B2 | * | 3/2004 | Wang et al. ................. 236/49.3 |
| 7,373,284 | B2 | * | 5/2008 | Stabelfeldt et al. ............. 703/2 |
| 2002/0062955 | A1 | * | 5/2002 | Dukes-Dobos et al. ...... 165/279 |
| 2002/0098761 | A1 | * | 7/2002 | Nishimoto et al. .......... 442/284 |
| 2002/0191669 | A1 | * | 12/2002 | Fan et al. ...................... 374/45 |
| 2003/0146290 | A1 | * | 8/2003 | Wang et al. ................. 236/49.3 |
| 2003/0189968 | A1 | * | 10/2003 | Lu et al. ....................... 374/45 |
| 2005/0086721 | A1 | * | 4/2005 | Lambertz ......................... 2/69 |
| 2007/0094763 | A1 | * | 5/2007 | Silver ............................. 2/69 |

OTHER PUBLICATIONS

E. A. Kim, S. Yoo, and J. Kim, "Development of a Human-Clothing-Environment Simulator for Dynamic Heat and Moisture Transfer Properties of Fabrics", vol. 4, No. 4,pp. 215-221, Fibers and Polymers 2003.*

H. S. Yoo, Y. S. Hu and E. A. Kim, "Effects of Heat and Moisture Transport in Fabrics and Garments Determined with a vertical Plate Sweating Skin Model", Textile Res. J. 70(6), 542-549 (2000).*

H. S. Yoo, Y. S. Hu, and E. A. Kim, "Effects of Heat and Moisture Transport in Fabrics and Garments Determined with a Vertical Plate Sweating Skin Model", Textile Res. J. 70(6), 542-549 (2000).*

X. Xu, and J. Werner, "A Dynamic Model of the Human/Clothing/Environment System", Jan. 6, 1997.*

E. Kim, et al.: "Development of Man-Clothing-Environment Simulator Manipulating Extreme Environmental Conditions," 7th Asian Textile Conference, New Delhi, India, Dec. 1-3, 2003, Synopsis, 3 pages.

E. Kim: "Newly Developed Skin Model; Human-Clothing-Environment Simulator," The Third International Conference on Human-Environment System, ICHES'05, Tokyo, Japan, Sep. 12-15, 2005, pp. 25-28.

E. Kim, et al.: "Application of Human-Clothing-Environment Simulator to Determine Comfort Properties at the Extreme and/or Transient Conditions," Thermal Manikins and Modeling, The Hong Kong Polytechnic University, 2006, pp. 268-277.

S. Yoo, et al.: "Effects of Multilayer Clothing System Array on Water Vapor Transfer and Condensation in Cold Weather Clothing Ensemble," Textile Research Journal, vol. 78, No. 3, pp. 189-197, 2008, http://trj.sagepub.com/cgi/content/abstract/78/3/189.

E. Kim, et al.: "Performance of Selected Clothing Systems under Subzero Conditions: Determination of Performance by a Human-Clothing-Environment Simulator," Textile Research Journal, vol. 76, No. 4, pp. 301-308, 2006, http://trj.sagepub.com/cgi/content/abstract/76/4/301.

* cited by examiner

HUMAN-CLOTHING-ENVIRONMENT SIMULATOR

BACKGROUND OF THE INVENTION

1. Field of the Invention

The present invention relates to a man-clothing-environment simulator quantitatively measuring capabilities of textile materials, such as clothing materials, to transfer heat and moisture between human skin and an external environment.

2. Description of the Related Art

A textile product is a porous aggregate of polymer materials with diverse physical and chemical structures, and its function is determined by properties of polymer materials, a structure of the aggregate, and an amount of air contained in the aggregate in a process of forming the aggregate. As the textile industry evolves into a high-tech industry, high value-added textile products with sophisticated functions are being developed. For clothing materials, comfort, texture, and sophisticated functions must be considered when producing high-value added clothing.

Comfort is often referred to as pleasantness, which is classified into thermal pleasantness and sensuous pleasantness. The thermal pleasantness is affected by a microclimate of an air layer formed between the body and clothes. The microclimate is determined by the capabilities of textile products to transfer heat and moisture generated by the human body. For general textile products, pleasantness related characteristics greatly affect consumers' preferences. When it comes to high-functional textile products used in special environments, the pleasantness related characteristics may even determine health and life of the human body.

Sensuous pleasantness refers to a way that a textile product feels when touched, such as soft, rough, warm, or cool, and determines the quality of the textile product. The sensuous pleasantness not only affects heat-and-humidity related characteristics but is also important for producing and evaluating highly sensuous textile products.

The capabilities of textile products to transfer heat and moisture are dependent upon comprehensive technology identifying and, by extension, quantifying interactions between the textile products and the human body as well as physical characteristics of polymers constituting the textile products and characteristics of an aggregate of polymers. In particular, it is necessary to develop a technology for measuring and evaluating heat/moisture transferring capabilities before developing high value-added textile products.

Conventional skin models used to measure the properties of clothing materials to transfer heat and humidity are usually disposed horizontally and designed to measure the properties under test conditions of standard state.

For example, U.S. Pat. No. 5,749,259 discloses a sweating hot plate apparatus for simulating thermoregulatory behavior of human skin. Since the sweating hot plate is disposed horizontally, it fails to properly simulate the relationship between clothes disposed vertically and the human body.

Micro-porous textile products, which are moisture-permeable and water-proof, have increasingly been used in sportswear and leisure wear. Under normal conditions, the micro-porous textile products can maintain moisture permeability. However, when they are used in the polar regions, moisture freeze in the fabric, thereby blocking micro-pores of the micro-porous textile products. Consequently, the intended moisture permeability of the micro-porous textile products disappears.

Therefore, it is important to be able to set test conditions in consideration of how and in what environment textile products are used. However, since conventional skin models measure moisture permeability at consistent temperature and humidity, they fail to fully reflect changes in the properties of textile products to transfer heat and moisture according to rapid environmental changes.

SUMMARY OF THE INVENTION

The present invention provides a man-clothing-environment (MCE) simulator using a vertical skin model to fully reflect a state of wearing clothes and measure properties of the clothes to transfer heat and moisture according to rapid environment changes.

According to an aspect of the present invention, there is provided an MCE simulator including a hot chamber providing a high-temperature environment; a cold chamber providing a low-temperature environment; a skin model selectively coupled to the hot chamber or the cold chamber while being vertically erect, the skin model including a hot plate receiving heat and water while being vertically erect and simulating human skin, a ring-shaped frame coupled to a side of the hot plate and supporting a fabric to be separated from the side of the hot plate, and sensors measuring temperature and humidity inside and outside the fabric; a water supplier supplying water to the hot plate; and a controller controlling the hot chamber, the cold chamber and the skin model, and processing data on temperature and humidity measured by the sensors.

The hot chamber and the cold chamber may be separated by a predetermined distance facing each other, and coupling apertures to which the skin model is coupled may be formed on respective surfaces of the hot chamber and the cold chamber that face each other. The skin model may include a cap attached to one of the coupling apertures, and the hot plate may be attached to one side of the cap.

The hot chamber may include a fan circulating internal air, a heater controlling internal temperature, a humidifier controlling internal humidity, and a sensor measuring the internal temperature and humidity. The cold chamber may include a fan circulating internal air, a cooler and a heater controlling internal temperature, and a sensor measuring the internal temperature.

The cold chamber may further include a humidifier controlling internal humidity and a sensor measuring the internal humidity. The water supplier may include a water supply tank storing water to be supplied and a water supply pump pumping the water to the hot plate.

The MCE simulator may include a skin model-supporting device interposed between the hot chamber and the cold chamber and supporting the skin model to be able to shuttle between the hot chamber and the cold chamber.

The skin model-supporting device may include a guide rail disposed between the hot chamber and the cold chamber, and the skin model may be suspended from the guide rail to be able to shuttle.

The hot plate may include a heater generating heat and a water-distributing plate attached to a side of the heater. The water-distributing plate may include a first plate attached to the side of the heater and have a plurality of water-distributing grooves formed on an outside surface of the first plate and a second plate closely attached to the outside surface of the first plate, and a plurality of penetrated water-distributing holes connected to the water-distributing grooves. A sweating layer spreading the water evenly may be attached to an outside surface of the water-distributing plate.

The skin model may include a ring-shaped spacer interposed between the hot plate and the frame to maintain a predetermined distance between the outside surface of the hot plate and the fabric. The sensor disposed inside the fabric may be supported by the spacer, and the sensor disposed outside the fabric may be supported by the frame.

The frame may include a plurality of frames and the frames may overlap and be coupled to one side of the hot plate. At least one opening corresponding to a neck or an arm of a human body may be formed in the frame.

The skin model may further include a cover to minimize loss of heat and moisture while moving between the hot chamber and the cold chamber.

The controller may include a control panel for controlling the hot chamber, the cold chamber and the skin model, and a computer processing the data on temperature and humidity measured by the sensors.

The MCE simulator according to the present invention can simulate a state of wearing clothes and effectively measure capabilities of the clothes to transfer heat and moisture according to rapid changes in an external environment.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
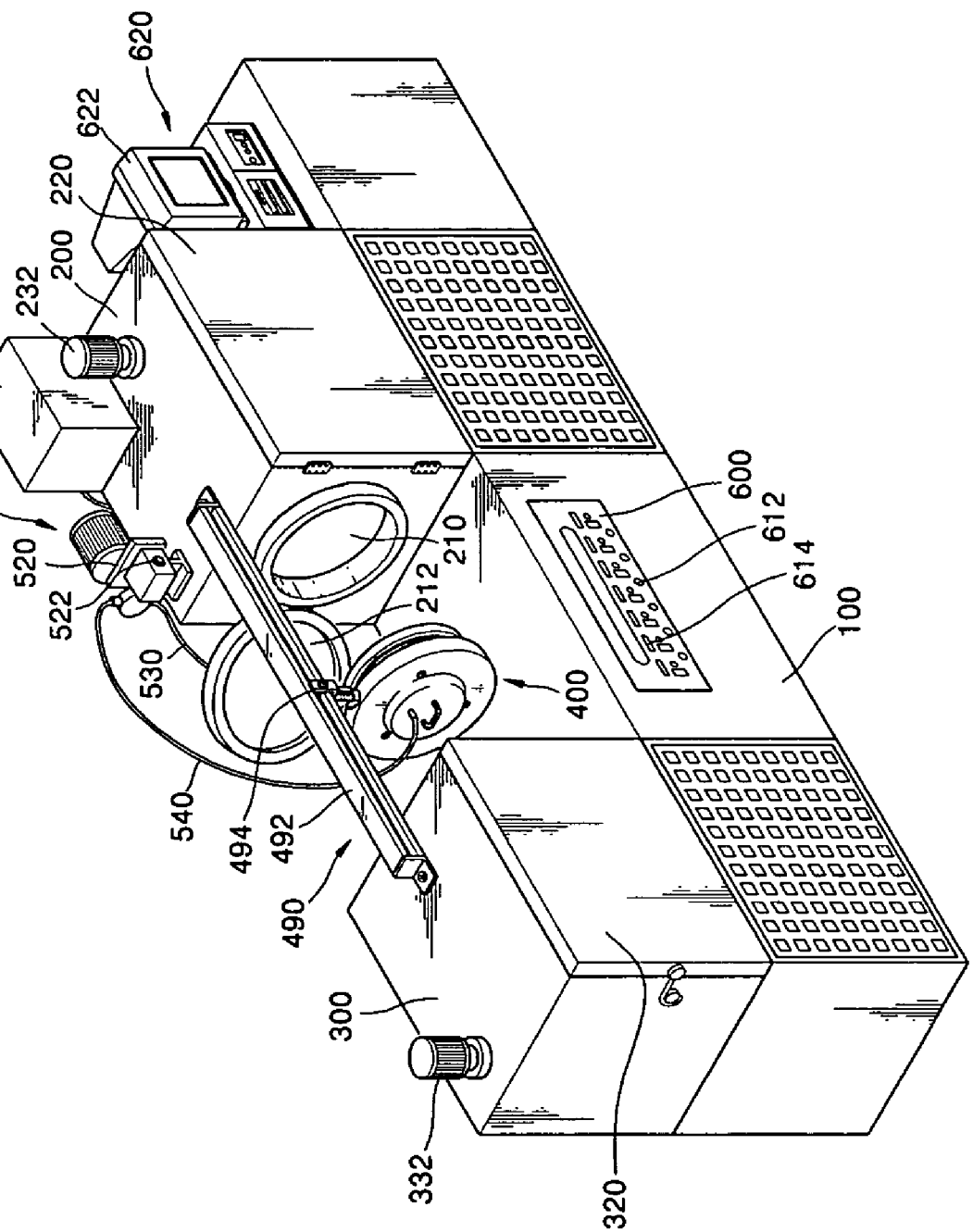
FIG. 1 is a perspective view of a man-clothing-environment simulator according to an embodiment of the present invention.

The present invention will now be described more fully with reference to the accompanying drawings, in which exemplary embodiments of the invention are shown. The invention may, however, be embodied in many different forms and should not be construed as being limited to the embodiments set forth therein; rather, these embodiments are provided so that this disclosure will be thorough and complete, and will fully convey the concept of the invention to those skilled in the art. Like reference numerals in the drawings denote like elements, and thus, their description will not be repeated.

Figure 2:
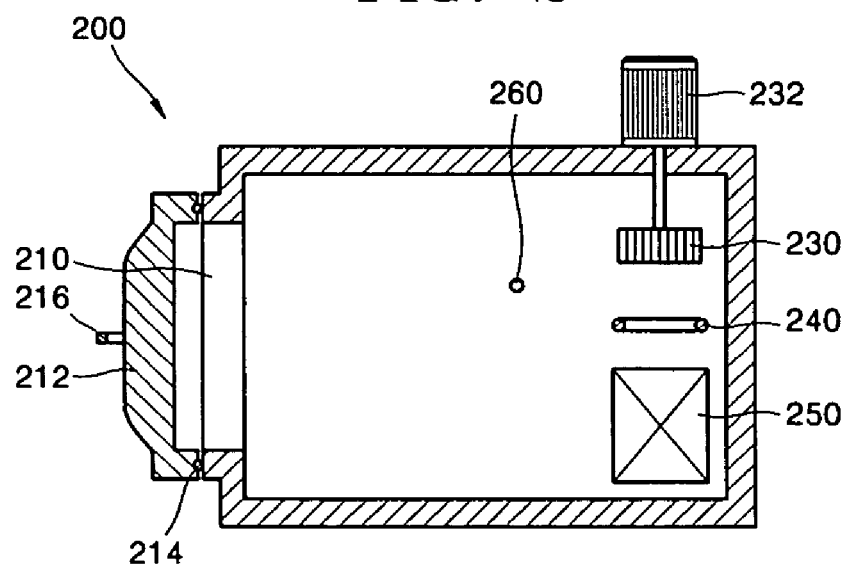
FIG. 2 is a vertical sectional view of a hot chamber illustrated in FIG. 1.
Figure 3:
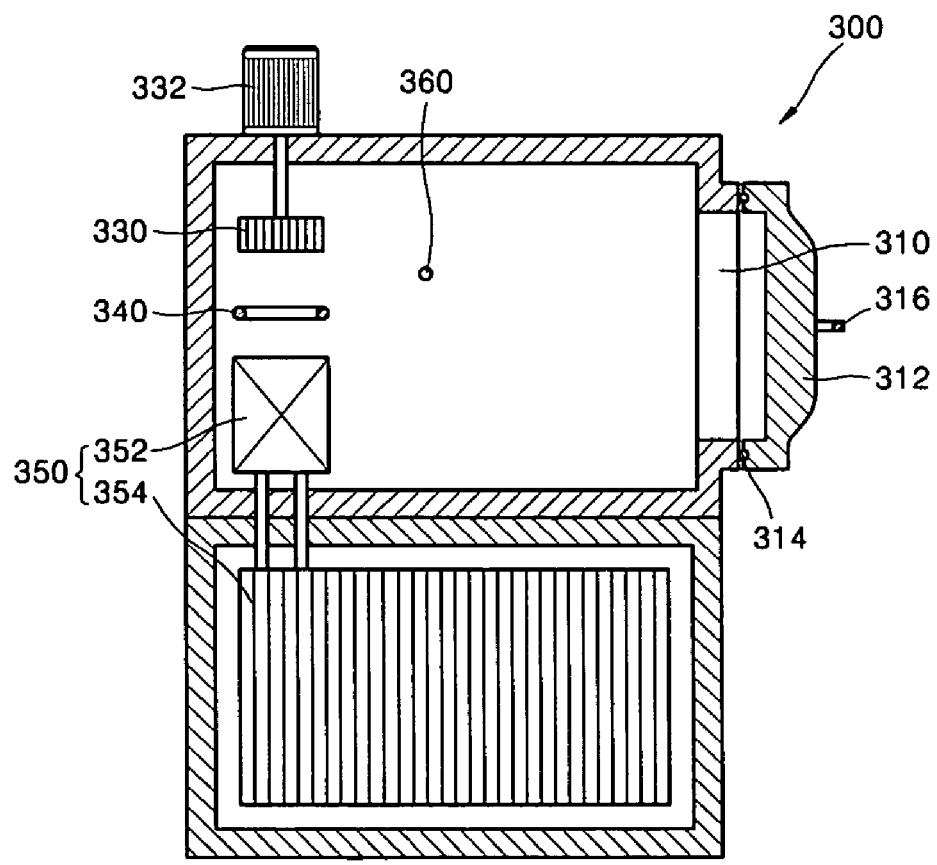
FIG. 3 is a vertical sectional view of a cold chamber illustrated in FIG. 1.

FIG. 1 is a perspective view of a man-clothing-environment simulator according to an embodiment of the present invention. FIG. 2 is a vertical sectional view of a hot chamber illustrated in FIG. 1. FIG. 3 is a vertical sectional view of a cold chamber illustrated in FIG. 1.

Referring to FIGS. 1 through 3, the man-clothing-environment (MCE) simulator measures how heat and sweat produced by the human body are released into the air through clothes that the human body is wearing in diverse environments, and estimates and evaluates pleasantness of the clothes.

Specifically, the MCE simulator quantitatively measures the properties of the clothes to transfer heat and moisture between human skin and an external environment. The MCE simulator includes a hot chamber 200, a cold chamber 300, a vertical skin model 400 simulating human skin, a water supplier 500 supplying water to the skin model 400, and a controller controlling the hot chamber 200, the cold chamber 300, and the skin model 400.

The hot chamber 200 provides a high-temperature environment to the skin model 400, and the cold chamber 300 provides a low-temperature environment to the skin model 400. The hot chamber 200 and the cold chamber 300 are disposed on opposite sides of a table 100 facing each other and separated by a predetermined distance. The skin model 400 is mounted on the table 100. Coupling apertures 210 and 310 to which the skin model 400 is coupled are formed in surfaces of the hot chamber 200 and the cold chamber 300, respectively, and face each other. The coupling apertures 210 and 310 are hinge-joined to doors 212 and 312, respectively, such that the coupling apertures 210 and 310 can be opened or closed. In addition, front doors 220 and 320 may be installed in the front of the hot chamber 200 and the cold chamber 300, respectively, to examine inside the hot and cold chambers 200 and 300.

The inside of the hot chamber 200 is controlled to maintain a hot and humid environment. The temperature of the hot chamber 200 may be raised up to, for example, approximately 50° C. above room temperature. To this end, the hot chamber 200 includes a heater 240 controlling temperature and a humidifier 250 controlling humidity. The humidifier 250 may be an evaporator generating water vapor by evaporating water supplied from a water supply tank 510 of the water supplier 500.

The hot chamber 200 may include a fan 230 circulating air to make uniform temperature and humidity in the hot chamber 200. The fan 230 is rotated by a fan motor 232 disposed on the hot chamber 200. Moreover, the hot chamber 200 may include a temperature/humidity sensor 260 measuring temperature and humidity. The temperature/humidity sensor 260 may be composed of a thermometer and a hygrometer either integrated or separated.

The inside of the cold chamber 300 is controlled to maintain a cold and dry environment. The temperature of the cold chamber 300 may be lowered down to, for example, approximately −30° C. below the room temperature. To this end, the cold chamber 300 includes a cooler 350 and a heater 340 for controlling the temperature. Mutually complementary operations of the cooler 350 and the heater 340 adjust the internal temperature of the cold chamber 300 to a desired level and maintains the internal temperature at the desired level.

The cold chamber 300 includes a refrigerant evaporator 352 of the cooler 350. A refrigerant condenser 354 is installed in a lower part of the cold chamber 300. The refrigerant evaporator 352 evaporates liquid refrigerant and lowers the internal temperature of the cold chamber 300 using latent heat of evaporation. The refrigerant condenser 354 condenses a gaseous refrigerant back into the liquid refrigerant by causing the gaseous refrigerant to radiate heat.

The cold chamber 300 may include a fan 330 circulating air to make uniform temperature and humidity in the cold chamber 300. The fan 330 is rotated by a fan motor 332 disposed on the cold chamber 300. The cold chamber 300 may also include a temperature sensor 360 measuring temperature.

The cold chamber 300 may include a humidifier controlling humidity similarly to the humidifier 250 of the hot chamber 200. In this case, a humidity sensor is installed within the cold chamber 300.

Handles 216 and 316 for easy handling may be attached to the doors 212 and 312 for opening or closing the coupling apertures 210 and 310 of the hot chamber 200 and the cold chamber 300, respectively. Sealing members 214 and 314 are disposed on contact surfaces of the coupling apertures 210 and 310 and the doors 212 and 312.

As described above, the MCE simulator according to the present invention includes the hot chamber 200 and the cold chamber 300. Since the skin model 400 can be sequentially coupled to the hot chamber 200 and the cold chamber 300, the MIC simulator can effectively measure the properties of clothes to transfer heat and moisture according to rapid changes in the external environment. In addition, the MCE simulator can effectively quantify the performance of functional textiles that are not identifiable under standard test conditions by expanding the test conditions to a temperature range of −30° C.-50° C.

Further, tests can be conducted under various environmental conditions in consideration of how and in what environment each product will be used. In particular, it is possible to conduct tests under extreme environmental conditions, where experiments on the human body are impossible, by adjusting the temperature and humidity of the external environment to extreme degrees.

Figure 4:
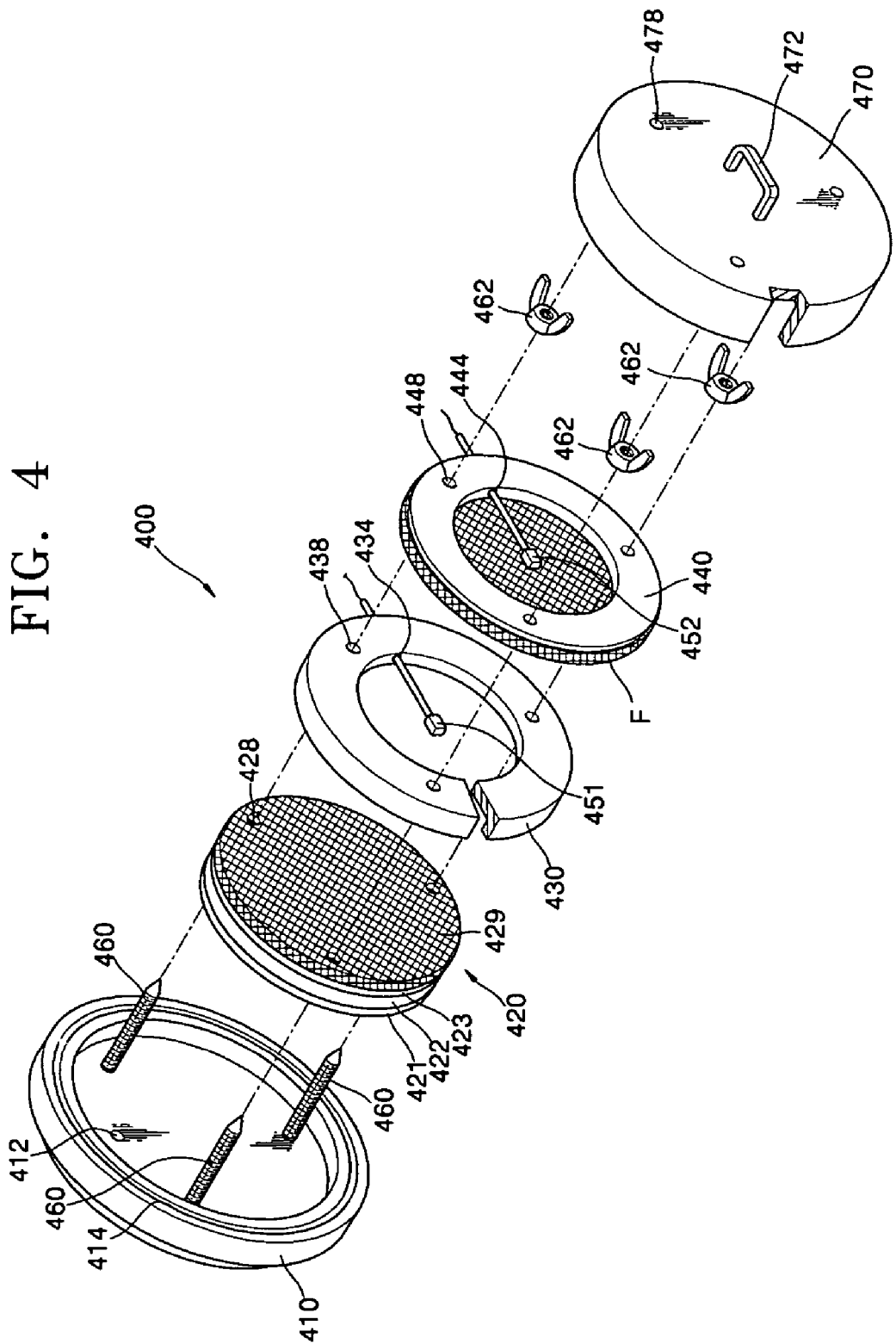
FIG. 4 is an exploded perspective view of a skin model of the simulator illustrated in FIG. 1.
Figure 5:
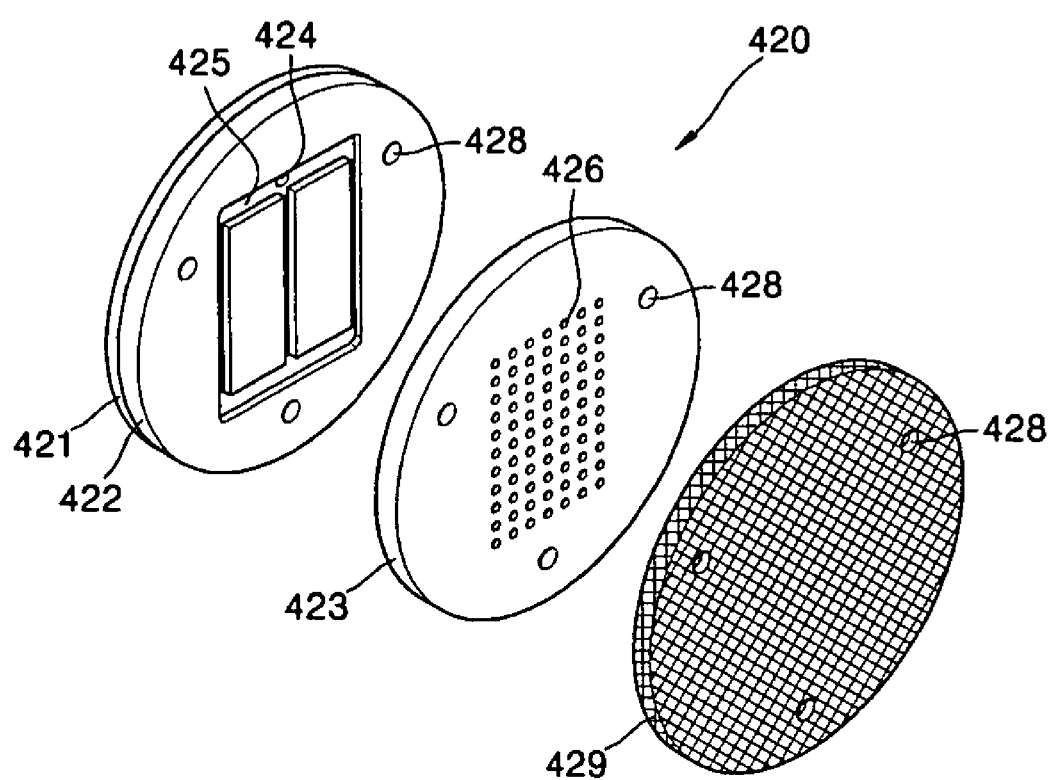
FIG. 5 is an exploded perspective view of a hot plate illustrated in FIG. 4.
Figure 6:
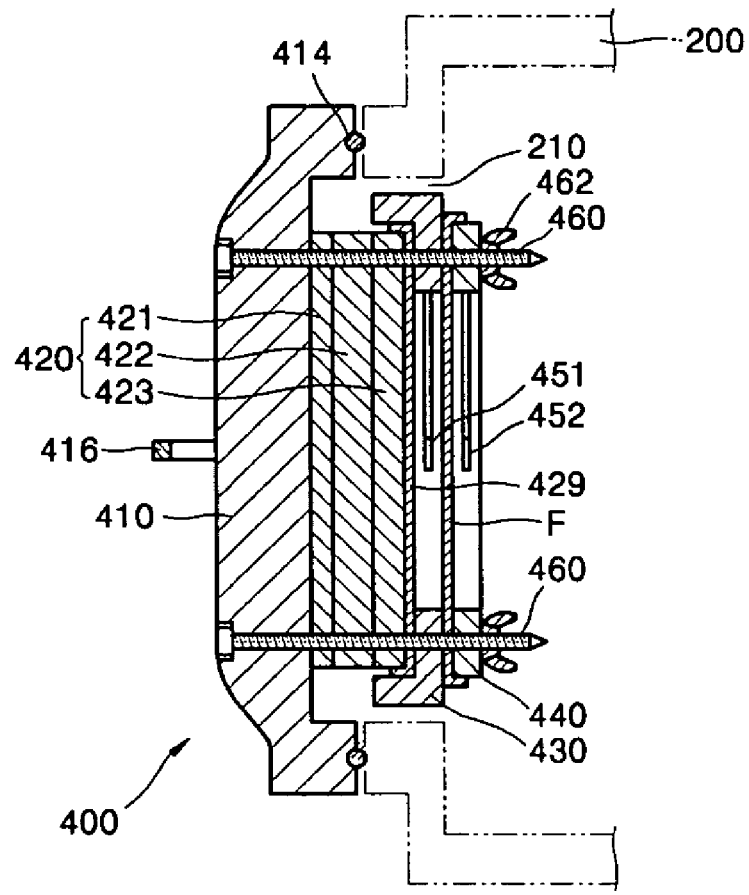
FIG. 6 is a sectional view of the skin model of FIG. 4 coupled to the hot chamber.

FIG. 4 is an exploded perspective view of the skin model 400 of the simulator illustrated in FIG. 1. FIG. 5 is an exploded perspective view of a hot plate 420 illustrated in FIG. 4. FIG. 6 is a sectional view of the skin model 400 of FIG. 4 coupled to the hot chamber 200.

Referring to FIGS. 1 and 4, the skin model 400 includes the hot plate 420, a ring-shaped frame 440, and a plurality of temperature/humidity sensors 451 and 452. The hot plate 420 receives heat and water in a vertically erect posture and simulates human skin. The ring-shaped frame 440 is coupled to a side of the hot plate 420 and supports a fabric F to be separated from the side surface of the hot plate 420. The temperature/humidity sensors 451 and 452 are disposed inside and outside the fabric F to measure temperature and humidity inside and outside the fabric F, respectively.

Since the skin model 400 is selectively coupled to the hot chamber 200 or the cold chamber 300 while being vertically erect, it may simulate a state of wearing clothes better than conventional horizontal skin models.

The skin model 400 may include a cap 410 attached closely to one of the coupling apertures 210 and 310 of the hot chamber 200 and the cold chamber 300. The hot plate 420 is attached to one side of the cap 410, and the sealing member 414 is installed along an edge of the one side of the cap 410. The cap 410 and the hot plate 420 may be coupled by a plurality of, for example, three, screws 460. To this end, a plurality of screw insertion holes 428 to which the screws 460 are inserted are formed in the hot plate 420. Further, a water supply hole 412 for supplying water to the hot plate 420 penetrates the cap 410 and is connected to a water supply hose 540 of the water supplier 500.

The hot plate 420 simulates the sweating human skin and is heated to maintain an average skin temperature. Water is supplied to the hot plate 420 through the water supply hole 412 such that the hot plate 420 contains a predetermined amount of moisture according to an amount of sweat. To this end, the hot plate 420 includes a heater 421 generating heat and a water-distributing plate attached to one side of the heater 421.

Referring to FIG. 5, the water-distributing plate includes a first plate 422 and a second plate 423. The first plate 422 is attached closely to one side of the heater 421 and includes a plurality of water-distributing grooves 425 formed on its outside surface and connected to a water supply hole 424. The water supply hole 424 is connected to the water supply hole 412 formed in the cap 410. The second plate 423 is attached closely to an outside surface of the first plate 422 and includes a plurality of water-distributing holes 426 connected to the water-distributing grooves 425. Therefore, water supplied through the water supply hole 424 is distributed along the water-distributing grooves 425 and spread onto an outside surface of the second plate 423 through the water-distributing holes 426.

A sweating layer 429 may be attached to the outside surface of the second plate 423 to spread the water evenly. Non-woven fabric or a variety of highly absorbent and easily dried fabrics that spread water rapidly and evenly and dry quickly may be used as the sweating layer 429. The screw insertion holes 428 into which the screws 460 are inserted may be formed in the first and second plates 422 and 423 and the sweating layer 429.

Referring back to FIG. 4, the ring-shaped frame 440 supporting the fabric F is coupled to one side of the hot plate 420. To this end, the screws 460 protrude from one side of the hot plate 420. A plurality of screw insertion holes 448 into which the screws 460 are inserted are formed in the frame 440. A ring-shaped spacer 430 may be interposed between the hot plate 420 and the frame 440 to maintain a predetermined distance between the outside surface of the hot plate 420 and the fabric F. In this case, a plurality of screw insertion holes 438 into which the screws 460 are inserted are formed in the spacer 430.

The temperature/humidity sensors 451 and 452 are disposed inside and outside the fabric F and are a temperature sensor and a humidity sensor either integrated or separated. The temperature/humidity sensor 451 disposed inside the fabric F measures temperature and humidity between the sweating layer 429 attached to the outside surface of the hot plate 420 and the fabric F supported by the frame 440. The temperature/humidity sensor 452 disposed outside the fabric F measures temperature and humidity outside the fabric F. The temperature/humidity sensor 451 is supported by the spacer 430, and the temperature/humidity sensor 452 is supported by the frame 440. To this end, the spacer 430 and the frame 440 include holes 434 and 444 that extend radially through their inner and outer circumferential surfaces, respectively. The temperature/humidity sensors 451 and 452 are inserted into and supported by the holes 434 and 444.

Referring to FIG. 6, the skin model 440 is formed by sequentially coupling the hot plate 420, the spacer 430, and the frame 440 to one side of the cap 410 and then connecting butterfly nuts 462 to the screws 460. The skin model 400 is coupled, for example, to the coupling aperture 210 of the hot chamber 200.

Referring to FIG. 4, a cover 470 may be used to minimize the loss of heat and humidity when the skin model 400 moves between the hot chamber 200 and the cold chamber 300. The cover 470 is composed of acrylic resin and covers circumferential and outside surfaces of the frame 440. The cover 470 also includes a handle 472 for easy handling and a plurality of screw insertion holes 478 into which end portions of the screws 460 may be inserted.

Figure 7:
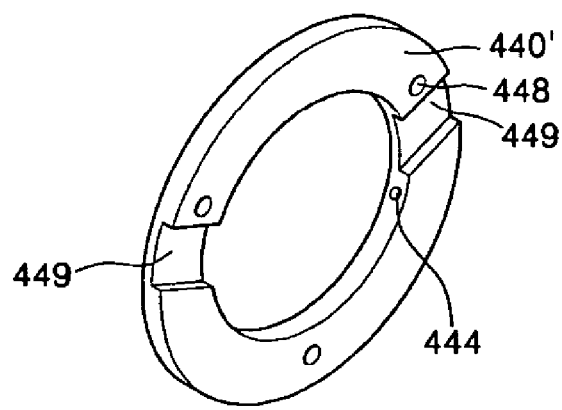
FIG. 7 is a perspective view of an alternative embodiment of the frame in FIG. 4.

FIG. 7 is a perspective view of an alternative embodiment of the frame in FIG. 4. Referring to FIG. 7, a plurality of openings 449 corresponding to the neck or an arm of the human body may be formed in the frame 440' supporting the fabric F. Accordingly, since the effects of openings formed in actual clothes can be quantitatively measured, the actual state of wearing the clothes may be properly reflected.

Figure 8:
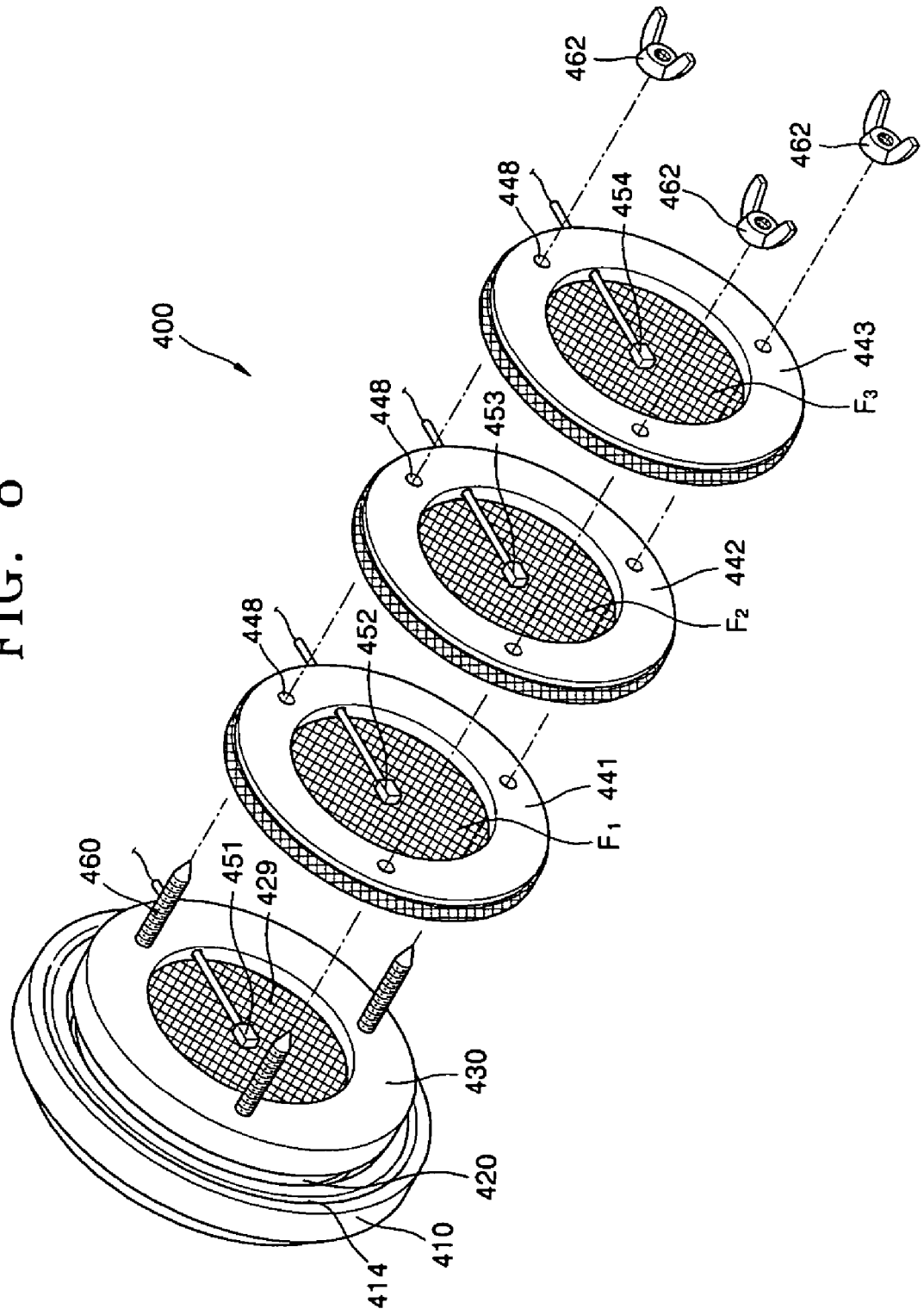
FIG. 8 is an exploded perspective view of the skin model of FIG. 4 including a plurality of frames according to an embodiment of the present invention.

FIG. 8 is an exploded perspective view of the skin model 400 of FIG. 4 including a plurality of frames 441, 442, and 443 according to an embodiment of the present invention. Referring to FIG. 8, the skin model 400 includes three frames 441, 442, and 443. Specifically, the frames 441, 442, and 443 overlap and are coupled to one side of the hot plate 420. If the spacer 430 is installed, the frames 441, 442, and 443 overlap and are connected to one side of the spacer 430.

The screw insertion holes 448 into which the screws 460 are inserted are formed in the frames 441, 442, and 443, respectively. Fabrics $F_1$, $F_2$, and $F_3$ are attached to one sides of the frames 441, 442, and 443, respectively. The frames 441, 442, and 443 also include temperature/humidity sensors 452, 453, and 454, respectively. In this way, if the skin model 400 includes the plurality of frames 441, 442, and 443, it is possible to measure the effect of wearing a plurality of clothes.

Referring back to FIG. 1, the water supplier 500 includes the water supply tank 510 storing water and a water supply pump 520 pumping water to the hot plate 420 of the skin model 400. The water supply tank 510 and the water supply pump 520 may be installed on the hot chamber 200. A metering pump may be used as the water supply pump 520 to supply a constant flow of water to the hot plate 420. In addition, a flow control valve controlling the quantity of water may be installed in the water supply pump 520. The water supply pump 520, the water supply tank 510, and the skin model 400 are connected by the water supply hoses 530 and 540.

Figure 9:
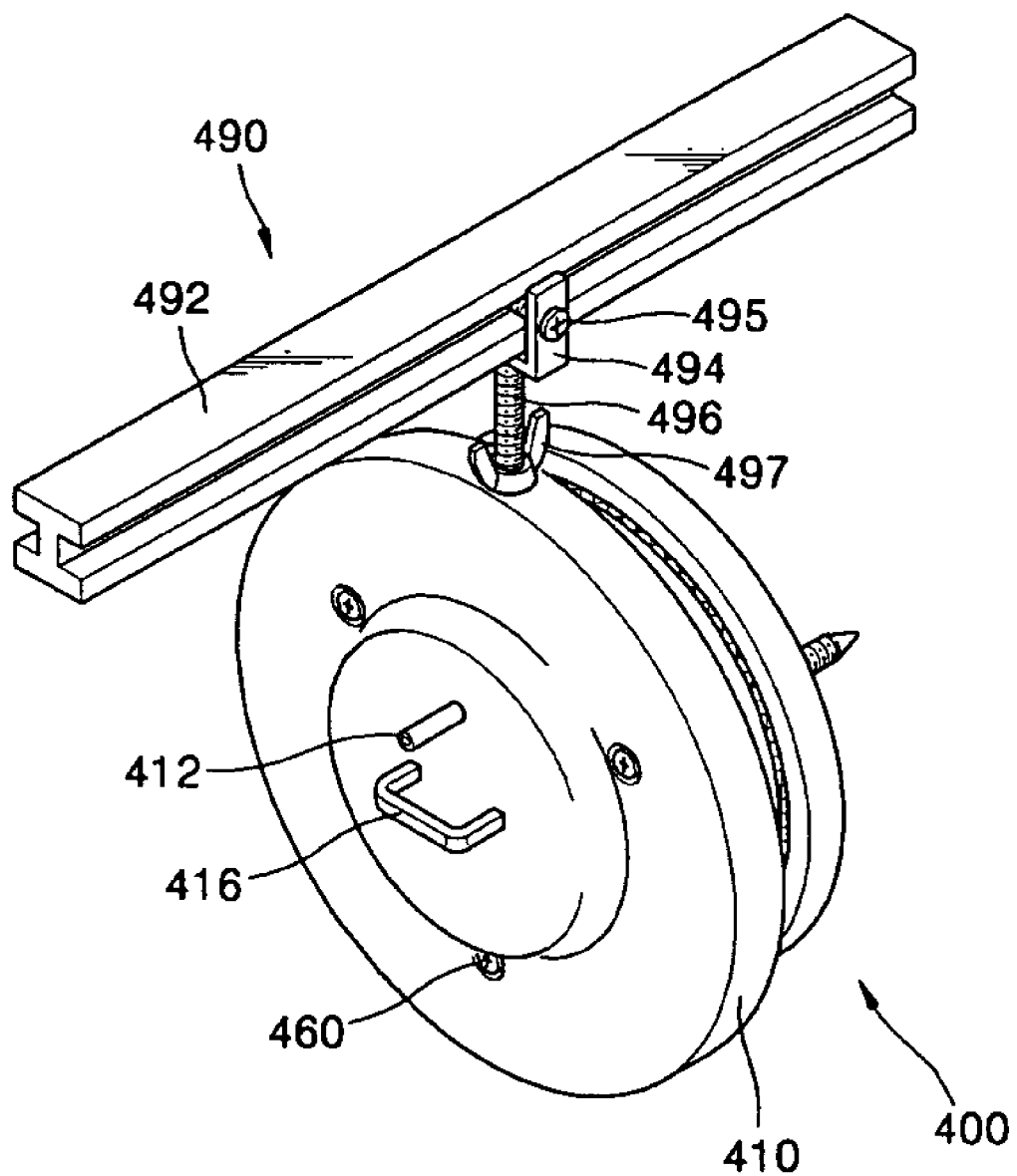
FIG. 9 is a perspective view of a skin model-supporting device illustrated in FIG. 1.

FIG. 9 is a perspective view of a skin model-supporting device illustrated in FIG. 1. Referring to FIGS. 1 and 9, the skin model-supporting device 490 supporting the skin model 400 to shuttle between the hot chamber 200 and the cold chamber 300 is interposed between the hot chamber 200 and the cold chamber 300. The skin model-supporting device 490 includes a guide rail 492 disposed between the hot chamber 200 and the cold chamber 300, and the skin model 400 is suspended from the guide rail 492 to be able to shuttle.

A bracket 494 is coupled to the guide rail 492 to slide along the guide rail 492, and a screw 496 for hanging the skin model 400 is coupled to the bracket 494. A screw 495 is coupled to the bracket 494, and the bracket 494 is attached to the guide rail 492 by the screw 495. The screw 496 is coupled to a top surface of the cap 410 of the skin model 400 and fastened by the butterfly nut 497. The cap 410 includes the handle 416 for easy handling of the skin model 400.

The skin model 400 can freely rotate about a vertical axis while hanging on the guide rail 492, and the skin model-supporting device 490 can change a direction of the skin model 400. Therefore, the skin model 400 can be selectively coupled to the coupling aperture 210 of the hot chamber 200 or the coupling aperture 310 of the cold chamber 300.

As described above, the skin model-supporting device 490 supports the vertical skin model 400, changes the direction of the skin model 400 to connect the skin model 400 to the hot chamber 200 or the cold chamber 300, and shuttles the skin model 400 between the hot chamber 200 and the cold chamber 300. Therefore, the skin model-supporting device 490 may have any structure including the structure illustrated in FIG. 9 as long as it performs the functions described above. For example, a turntable that can shuttle between the hot and cold chambers 300 and 200 may be disposed on the table 100, and the skin model 400 may be disposed on the turntable.

In addition, a space between the hot chamber 200 and the cold chamber 300 may be a closed space, and the skin model 400 may shuttle automatically between the hot chamber 200 and the cold chamber 300. In this case, a variety of well-known conventional driving devices may be used to automatically shuttle the skin model 400. For example, the turntable supporting the skin model 400 may be disposed on the table 100, and the turntable may be shuttled by a lead screw, and the lead screw may be automatically controlled by the controller.

Referring to FIG. 1, the controller includes a control panel 600 for controlling the hot and cold chambers 200 and 300 and the skin model 400, and a computer 620 processing temperature and humidity measured by the sensors 450 and 460 included in the skin model 400. The control panel 600 is disposed on the front of the table 100 and includes a plurality of control switches 612 and a temperature/humidity display 614. The computer 620 stores data on the temperature and humidity measured in the skin model 400 and quantifies the properties of a fabric, for example, clothing, to transfer heat and moisture based on the data. The quantified properties of the clothing to transfer heat and moisture may be displayed on a monitor 622.

As described above, it is possible to measure, in an integrated manner, the feeling, performance, and pleasantness of textile products worn on the human body, such as clothes, decorative textiles including sofa covers and carpets, car sheets, bed sheets, or textile products for medical purposes, according to environments in which the textile products are used by using the MCE simulator according to the present invention. Simulation results are verified by experiments on a mannequin or the human body, and the importance and weight of each factor can be determined according to the expected usage of the material to estimate comfort levels of the textile products.

Since the pleasantness and performance of the textile products are evaluated and estimated in actual states of wearing the textile products, it is possible to estimate user satisfaction levels, effects of the textile products on the human body, and the feasibility of developing the textile products. In addition, since the MCE simulator is used when developing and planning fabrics, textile products that can meet the needs of customers can be produced. The MCE simulator also provides evaluation indices for pleasantness, which may be used for standardizing the textile products.

As described above, an MCE simulator according to the present invention may properly simulate a state of wearing clothes by employing a vertical skin model. The MCE simulator includes two chambers providing high-temperature and low-temperature environments, respectively, thereby effectively measuring properties of clothes to transfer heat and moisture according to rapid changes in an external environment. In addition, since a plurality of frames supporting a fabric can be used, the effect of wearing a plurality of clothes may be measured. Further, since openings corresponding to the neck or the arm of the human body can be formed in the frames, it is possible to measure their effects.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A human-clothing-environment simulator for quantitatively measuring properties of clothes to transfer heat and moisture between human skin and an external environment, the simulator comprising:

a hot chamber providing a high-temperature external environment to which human skin and a fabric are exposed;

a cold chamber providing a low-temperature external environment to which human skin and fabric are exposed;

a skin model selectively coupled to the hot chamber or the cold chamber while being vertically erect, the skin model comprising:
- a hot plate receiving heat and water while being vertically erect and simulating human skin;
- a ring-shaped frame coupled to a side of the hot plate and supporting a fabric to be separated from the side of the hot plate; and
- at least one sensor measuring temperature and humidity between the hot plate and the fabric; and
- at least one sensor measuring temperature and humidity outside the fabric;

a water supplier supplying water to the hot plate;

a controller controlling the hot chamber, the cold chamber and the skin model, and processing data on temperature and humidity measured by the sensors; and a skin model-supporting device interposed between the hot chamber and the cold chamber and supporting the skin model to be able to shuttle between the hot chamber and the cold chamber; and wherein the hot chamber and the cold chamber are separated by a predetermined distance, and coupling apertures are formed on respective surfaces of the hot chamber and the cold chamber that face each other; and wherein the skin model-supporting device comprises a guide rail disposed between the hot chamber and the cold chamber, and the skin model is suspended from the guide rail to be able to shuttle the simulator.

2. The simulator of claim 1, wherein the skin model comprises a cap attached to one of the coupling apertures, and the hot plate is attached to one side of the cap.

3. The simulator of claim 2, wherein the cap and the hot plate are coupled by a plurality of screws, the screws protruding from one side of the hot plate, and a plurality of screw insertion holes into which the screws are inserted are formed in the frame.

4. The simulator of claim 1, wherein the hot chamber comprises a fan circulating internal air, a heater controlling internal temperature, a humidifier controlling internal humidity, and a sensor measuring the internal temperature and humidity.

5. The simulator of claim 1, wherein the cold chamber comprises a fan circulating internal air, a cooler and a heater controlling internal temperature, and a sensor measuring the internal temperature.

6. The simulator of claim 5, wherein the cold chamber further comprises a humidifier controlling internal humidity and a sensor measuring the internal humidity.

7. The simulator of claim 5, wherein the cooler comprises a refrigerant evaporator installed inside the cold chamber and a refrigerant condenser installed in a lower part of the cold chamber.

8. The simulator of claim 1, wherein the water supplier comprises a water supply tank storing water to be supplied and a water supply pump pumping the water to the hot plate.

9. The simulator of claim 1, wherein the skin model can rotate about a vertical axis while being suspended from the guide rail.

10. The simulator of claim 1, wherein the hot plate comprises a heater generating heat and a water-distributing plate attached to a side of the heater.

11. The simulator of claim 10, wherein the water-distributing plate comprises a first plate attached to the side of the heater and has a plurality of water-distributing grooves formed on an outside surface of the first plate and a second plate closely attached to the outside surface of the first plate, and a plurality of penetrated water-distributing holes connected to the water-distributing grooves.

12. The simulator of claim 10, wherein a sweating layer spreading the water evenly is attached to an outside surface of the water-distributing plate.

13. The simulator of claim 12, wherein the sweating layer is composed of a highly absorbent and easily dried fabric.

14. The simulator of claim 1, wherein the skin model comprises a ring-shaped spacer interposed between the hot plate and the frame to maintain a predetermined distance between the outside surface of the hot plate and the fabric.

15. The simulator of claim 14, wherein the sensor disposed inside the fabric is supported by the spacer, and the sensor disposed outside the fabric is supported by the frame.

16. The simulator of claim 15, wherein holes penetrating the spacer and the frame, extending from outer circumferential surfaces to inner circumferential surfaces, are formed in the spacer and the frame, respectively, and the sensors are inserted into and supported by the holes.

17. The simulator of claim 1, wherein the frame comprises a plurality of frames and the frames overlap and are coupled to one side of the hot plate.

18. The simulator of claim 1, wherein at least one opening corresponding to a neck or an arm of a human body is formed in the frame.

19. The simulator of claim 1, wherein the skin model further comprises a cover to minimize loss of heat and moisture while moving between the hot chamber and the cold chamber.

20. The simulator of claim 1, wherein the controller comprises a control panel for controlling the hot chamber, the cold chamber and the skin model, and a computer processing the data on temperature and humidity measured by the sensors.

21. The simulator of claim 1, wherein an internal temperature of the hot chamber is in the range of between about room temperature and about 50° C.

22. The simulator of claim 1, wherein an internal temperature of the cold chamber is in the range of between about room temperature and about −30° C.

* * * * *